United States Patent
Jalali et al.

(10) Patent No.: US 10,711,786 B2
(45) Date of Patent: Jul. 14, 2020

(54) EMBEDDED ROTARY MICRO PUMP, ITS METHOD OF INTEGRATION AND MOTION CONTROL

(71) Applicant: Micromotion Systems LLC, Sunnyvale, CA (US)

(72) Inventors: Mir Abbas Jalali, Palo Alto, CA (US); S Abbas Hosseini, Los Altos, CA (US); Amir Tork, Quebec (CA)

(73) Assignee: Citroqene, Inc, San Jose, CA (US)

( * ) Notice: Subject to any disclaimer, the term of this patent is extended or adjusted under 35 U.S.C. 154(b) by 192 days.

(21) Appl. No.: 15/900,123

(22) Filed: Feb. 20, 2018

(65) Prior Publication Data

US 2018/0238333 A1     Aug. 23, 2018

Related U.S. Application Data

(60) Provisional application No. 62/461,982, filed on Feb. 22, 2017.

(51) Int. Cl.
    *F04D 5/00*    (2006.01)
    *F04D 13/06*   (2006.01)
    *F04B 19/00*   (2006.01)

(52) U.S. Cl.
    CPC .............. *F04D 5/001* (2013.01); *F04D 13/06* (2013.01); *F04B 19/006* (2013.01)

(58) Field of Classification Search
    CPC ........ F04D 5/001; F04D 13/06; F04D 17/161; F01D 1/36; F05D 2260/408
    USPC ............................................... 415/90
    See application file for complete search history.

(56) References Cited

U.S. PATENT DOCUMENTS

| | | | |
|---|---|---|---|
| 5,788,468 A * | 8/1998 | Dewa ............... | F04B 43/043 417/410.3 |
| 2007/0059156 A1* | 3/2007 | Blanchard .......... | F04D 1/02 415/90 |

\* cited by examiner

*Primary Examiner* — Philip E Stimpert
(74) *Attorney, Agent, or Firm* — Frijouf, Rust & Pyle P.A.

(57) ABSTRACT

A micro pumping mechanism is proposed to generate flow in micro channels of micro fluidic devices and three dimensional microprocessors cooled by the flow of coolant fluids. The proposed micro pump comprises a rotating disk inside a chamber, which overlaps with the fluidic micro channel. The rotating disk induces a shear flow across the micro channel, transporting fluid elements in the direction of the rotation of the disk. The disk can be rotated by external magnetic or electric fields as in direct drive, induction, or electrostatic motors.

16 Claims, 3 Drawing Sheets

EMBEDDED ROTARY MICRO PUMP, ITS METHOD OF INTEGRATION AND MOTION CONTROL

CROSS-REFERENCE TO RELATED APPLICATIONS

This application claims benefit of U.S. Provisional Patent application No. 62/461,982 filed 22 Feb. 2017. All subject matter set forth in provisional application No. 62/461,982 filed 22 Feb. 2017 is hereby incorporated by reference into the present application as if fully set forth herein.

BACKGROUND OF THE INVENTION

Field of the Invention

This invention relates to rotary pumps and more particularly to an embedded rotary micro pump.

Description of the Related Art

Fluid pumping in micro channels is a technological challenge because in sub-millimeter scales viscous forces dominate inertial ones and most conventional pumping methods based on periodic movements of mechanical actuators fail. Flow generation in micro channels is achieved by two general classes of pumps: (i) external pumps and (ii) integrated pumps. Widely-used external pumps are pressure, vacuum, and syringe pumps, which can induce continuous and steady flow rates. Most Integrated pumps are non-mechanical, including electroosmotic and electrowetting pumps that have been devised for continuous-flow micro fluidics and droplet handling devices. Flexible diaphragms actuated by pressure, vacuum or piezoelectric actuators, and peristaltic pumps are mechanical systems that can be used both as external and integrated pumps. Capillary pumps are another class of integrated pumps. Capillary pumps work based on the wetting characteristics of the fluid and substrate, and are categorized as non-mechanical pumps.

Most micro fluidic platforms in molecular biology, DNA analysis, sequencing, proteomics, diagnosis and point-of-care medicine handle minuscule amounts of fluid samples (e.g., blood). Removing connections to external pumps and fabricating on-chip pumps is a key step in most of these applications and paves the path for the development of low-cost integrated chips. Easy operation is another crucial requirement, which can be fulfilled by integrated pumps. Current on-chip pumps mostly work based on electrowetting and electroosmosis. However, the efficiency of devices that utilize electrowetting for the handling of fluids or droplets highly depends on the fluid's surface tension properties, viscosity and how the fluid responds to an electric potential field. For example, the addition of proteins and other biological material to samples can significantly change the surface tension properties and reduce the efficiency of the device. Moreover, the application of electroosmotic pumps is limited to conducting liquids and these pumps suffer from permittivity, zeta, and bubble formation problems. In digital PCR (Polymerase Chain Reaction) applications where droplets of water-based samples are carried by non-conducting and non-polar oil and various surfactants are present in the mixture, electroosmotic and electrowetting techniques would fail.

Therefore, it is an object of the present invention to provide an improved a simple, scalable, ultra-low-cost, on-chip mechanism that pumps all kinds of fluids and any viscosity through micro channels.

Another object of the present invention is to provide a micro rotary pumping system for pumping a fluid though the use of an external rotating magnetic field.

Another object of the present invention is to provide a micro rotary pumping system for pumping a fluid only by shearing a portion of the fluid within a micro channel.

Another object of the present invention is to provide a micro rotary pumping system for pumping a fluid incorporating an annular disk that is embedded and sealed in a substantially cylindrical chamber.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an improved micro rotary pumping system for pumping a fluid though the use of an external rotating magnetic field. The micro rotary pumping comprises a micro channel for directing the fluid. A chamber is located adjacent to the micro channel in fluid communication with the micro channel. An annular disk is located in the chamber. A magnetic material affixed to the annular disk and magnetically coupled to the external rotating magnetic field for rotating the annular disk to create a shear in the fluid in the micro channel for pumping the fluid thereby.

In a more specific example, the chamber is substantially cylindrical chamber and the micro channel intersecting a peripheral region of the cylindrical chamber. The annular disk is embedded and sealed in the substantially cylindrical chamber. The chamber has a longitudinal axis perpendicular to an axis of rotation of the annular disk.

In another specific example, the annular disk defines a substantially smooth cylindrical circumference. The annular disk is void of a rotational axel and is rotationally stabilized by the fluid between the annular disk and the chamber. Preferably, the annular disk has a diameter between 10 micrometer and 10 millimeters. In one example, the magnetic material affixed to the annular disk comprises a permanent magnet. In another example, the magnetic material affixed to the annular disk comprises an elongated ferromagnetic core The invention also resides in the method of pumping a fluid in a micro channel. The method comprises the steps of rotating an annular disk within a sidewall of the micro channel for exerting boundary shear stress on the fluid along the micro channel to induce a velocity gradient across the channel and generates fluid flow. Preferably, the step of rotating the annular disk includes magnetically coupling the annular disk to an external rotating magnetic field for rotating the annular disk.

It has been discovered that a single, or a group of circular disks, which spin about their symmetry axes, can pump fluids in micro channels. Each disk is installed at the boundary of the micro channel and exerts boundary shear stress on the fluid along the channel. The boundary shear induces a velocity gradient across the channel and generates fluid flow. Sufficiently far from the rotating disk the flow evolves to a laminar flow. The flow generated by this mechanism is steady and continuous without any pulses. The pumping mechanism proposed in this invention does not depend on the properties of the fluid. All fluids regardless of their viscosity and molecular properties can be pumped. Depending on the required shear force for pumping, the disks can be rotated by external magnetic or electric fields. The diameters and thicknesses of the disks can vary from tens of micrometers to a few millimeters. The disks are embedded and sealed in micron-scale chambers, and devices composed of these disks and micro fluidic circuits are disposable. Integrated micro pumps proposed here can also be applied to microprocessor cooling. The micro pumps can continuously and efficiently pump coolant fluids through micro channels in two and three-dimensional microprocessors. The flow rate can be smoothly controlled by varying the rotational speed of the disk.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which.

Similar reference characters refer to similar parts throughout the several Figures of the drawings.

DETAILED DISCUSSION

The present invention provides a method and an apparatus to generate fluid flow in micro channels. Pressure-driven fluid flow in straight micro channels is laminar where fluid elements move along straight lines. Across the channel cross section, however, the streaming velocity varies due to shear stresses between fluid layers. Fluid elements near channel walls have smaller speeds than those moving at or near the channel centerline. In the idealistic case of no-slip boundary conditions (zero velocity at the walls) and in a channel of circular cross section, the flow profile is parabolic. In such conditions, fluid elements at the channel centerline have the maximum speed.

Figure 1:
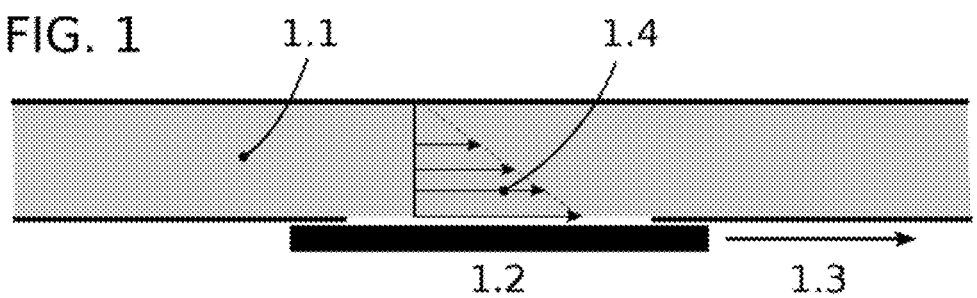
FIG. 1 presents a schematic view of shear-induced flow in a micro channel. Fluid 1.1 inside the micro channel is sheared by wall 1.2 that moves along arrow 1.3. Consequently, a velocity field similar to 1.4 is generated across the channel. This mechanism transports mass and generates flow.

FIG. 1 illustrates a micro channel filled the fluid 1.1. In the absence of any pressure gradient along the channel, if one of the walls (e.g., wall 1.2) moves parallel to the channel centerline in the direction 1.3, a shearing layer will be created at the channel's boundary generating velocity profile 1.4. This mechanism will transport mass and generate flow along the channel. However, sustaining continuous movement of wall 1.2 to generate a steady flow through this mechanism is impractical. This problem is solved by locally and continuously shearing the fluid inside the micro channel.

Figure 2:
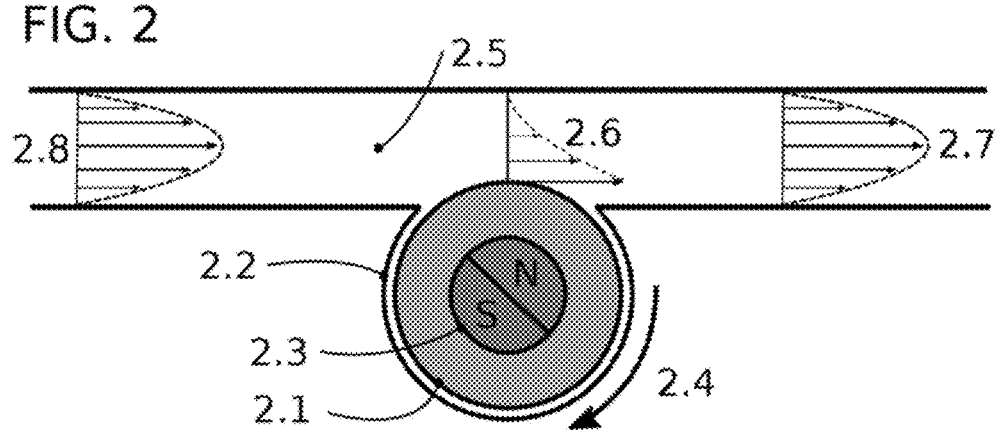
FIG. 2 presents a schematic view of the shear pump system comprising an annular disk 2.1 that spins inside closed chamber 2.2. A permanent diametrically magnetized magnet 2.3 is installed at the center of the disk. A disk rotating clockwise, as shown by arrow 2.4, generates the flow field 2.6 in the space between disk 2.1 and main micro channel 2.5. Upstream and downstream flow fields marked as 2.7 and 2.8, respectively, are laminar.

FIG. 2 illustrates the pump of the present invention, comprising a disk 2.1 that rotates within a closed chamber 22. The rotation direction 2.4 has been shown by an arrow. A diametrically magnetized permanent disk magnet 2.3 is installed at the center of the disk. The rotor comprises the combination of the disk 2.1 and the central magnet 2.3. Using contactless, brushless, external magnetic fields induced either by a rotating permanent magnet or an array of coils levitates rotor inside chamber 2.2 at a high angular speed. Chamber 2.2 and main micro channel 2.5 overlap and are filled with fluid when the rotor spins. As the rotor spins, it generates a shearing layer with a profile similar to 2.6. Fluid particles near the rotor follow its velocity and the ones close to the wall of the main channel remain at rest. Consequently, the fluid trapped between the rotor and channel walls is transported along the channel. As fluid elements move in micro channel 2.5, the flow in the downstream becomes laminar with a profile similar to 2.7. The flow profile 2.8 in the upper stream is also laminar.

As the rotor spins, hydrodynamic forces exerted by the fluid filling the gap between rotor and chamber 2.2 radially stabilize the rotor pushing it away from chamber walls. Another aspect of the present invention and a determining factor for the operation of the pump is the size of the gap between chamber 2.2 and rotor. The smaller the gap, the larger the radially stabilizing hydrodynamic forces. Moreover, the rotor's spin becomes more stable when the overlap between chamber 2.2 and micro channel 2.5 is small. The flow generated by the pump is smooth, noiseless and has no pulses. The larger the rate of spin of the disk, the bigger the velocity of fluid elements and the larger the induced flow rate. Sufficiently far from the rotor both in the upstream and downstream sides, fluid flow is steady and laminar. Near the rotor, however, some local vortices may appear generating turbulence and mixing. Despite its rotational nature, the micro pumping mechanism of this invention does not work based on centrifugal forces. This makes present pumps distinct from all existing rotary pumps that accelerate fluid particles using centrifugal forces. The pumps of this invention are also distinct from gear micro pumps. Gear micro pumps need to operate in pairs while they compress fluid elements and any suspension particles between contacting gears. The present micro pumping mechanism only shears fluid elements and does not compress suspension particles against another part of the channel.

As the rotational speed of the rotor increases, resistive hydrodynamic shear forces increase as well. This requires stronger engagement of external magnetic fields with the permanent disk magnet 2.3 and increases the power required for spinning the rotor. Nonetheless, since the driving mechanism is brushless and the rotor spins inside a chamber filled by fluid, momentum loss due to dry friction and subsequent heating are minimal. Noise level also remains at a minimum. These properties are favored not only in biochips operated in thermal equilibrium but also in microprocessor cooling where the heat and noise generated by the cooling system should be minimized. The quiet and pulseless pumping mechanism proposed here is suitable for three dimensional microprocessors and Integrated Circuits (IC), which are cooled by the flow of liquid or polymeric coolants.

Typically, the micro channel 2.5 can range from 5 µm to 500 µm wide whereas the chamber 2.2 can range from 100 µm to 10 mm in diameter. Preferably, the annular disk 2.1 generally has 20 µm less diameter than chamber 2.2 to provide a 10 µm clearance between the annular disk 2.1 and the chamber 2.2. In one example, an integrated circuit has 100 µm micro channel 2.2 and a 2 mm diameter chamber 2.2.

Description of the Mechanisms of Spinning the Rotor

Figure 3:
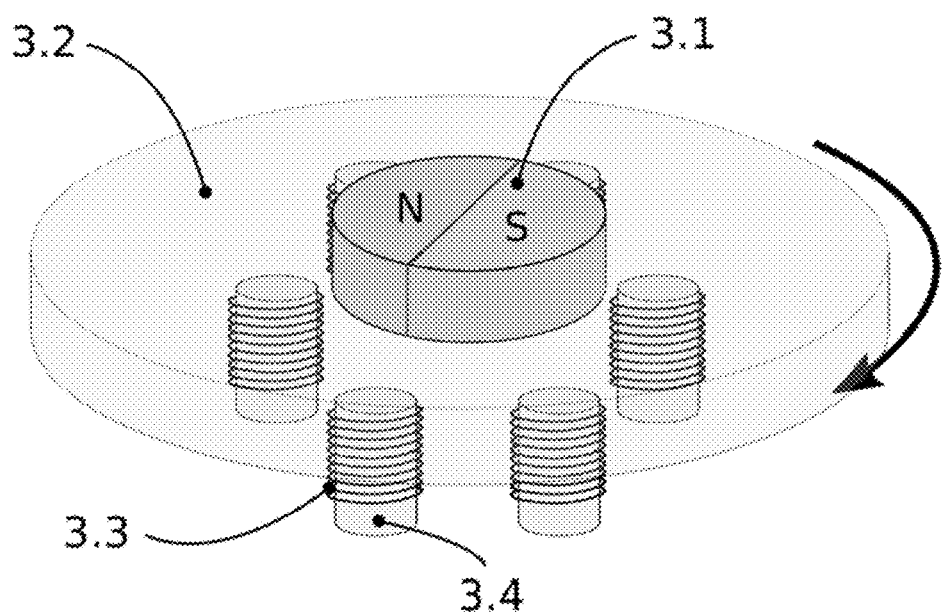
FIG. 3 presents a schematic view of the rotor, comprising a diametrically permanent magnetized disk magnet 3.1 which is installed in and fixed to annular disk 3.2, and a hexagonal array of six identical coils. Each coil 3.3 has been wrapped around a ferromagnetic core 3.4. The axis and core of each coil are directed towards the rotor's central disk magnet.

The rotor with a diametrically magnetized permanent disk magnet can be actuated in a contactless manner by two general methods: (i) an array of coils as shown in FIG. 3, or (ii) a rotating permanent magnet as in FIG. 4.

In method (i), to simultaneously levitate and rotate a diametrically magnetized permanent disk magnet of the rotor, a minimum of four coils are required: two coils shall levitate and repel the rotor and two other coils attract it. A smoother and more accurate performance depend on the number of the coils. A deliberately designed periodic signal passes through the coils so that there are at least one coil pair that repels (levitates) the rotor and at least one coil pair that attracts the rotor. With six coils, for example, it is also possible to simultaneously repel the rotor by three pairs and attract it by the other three pairs. Each actuating coil 3.3 of FIG. 3 has a ferromagnetic core 3.4 which is designed to align the magnetic field bundle of each coil towards the rotor.

Figure 4:
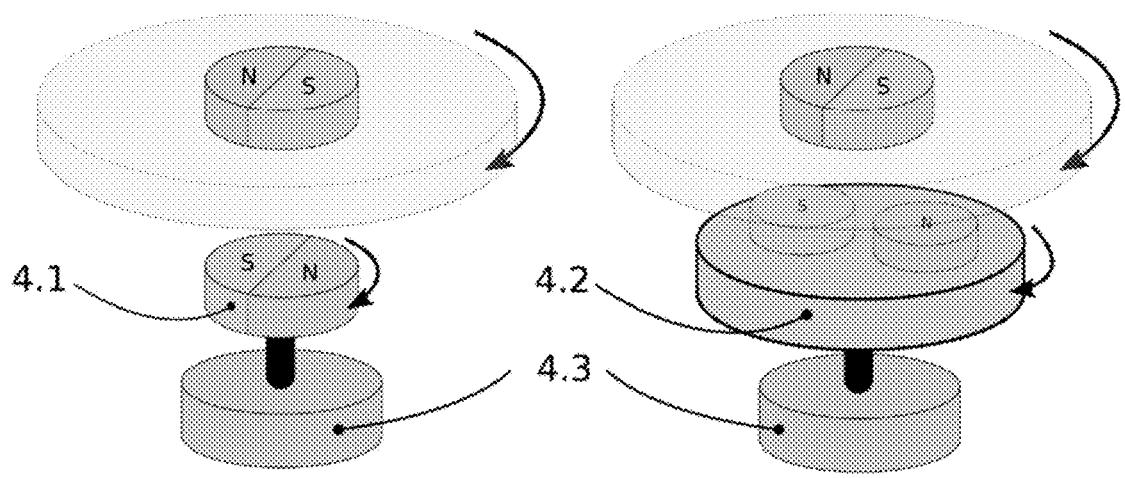
FIG. 4 presents a schematic view of the rotor spun by a magnetic clutch (coupling). The magnetic clutch can be a single diametrically magnetized disk magnet 4.1 or a set of axially magnetized disk magnets 4.2. The clutch is rotated by an external motor 4.3. There is no direct contact between the magnet of the rotor and the magnets of the clutch.

In method (ii), the rotor is spun using a magnetic clutch as shown in FIG. 4. The magnetic clutch can be a diametrically magnetized disk magnet 4.1 or a set of two (or more) axially magnetized disk magnets 4.2 rotated by an external motor 4.3. The main advantage of this method is its easy implementation using off-the-shelf motors, but due to the attractive force between the rotor and clutch magnets, the rotor is not levitated (either magnetically or hydrodynamically) inside the chamber. Consequently, one side of the rotor that faces the clutch directly contacts the chamber, generating dry friction and noise.

Disk 2.1 of the present invention can be rotated without using the permanent magnet 2.3. For example, replacing the magnet by a millimeter or sub-millimeter scale electrically conducting squirrel cage and using a three-phase coil magnet system (through which a pulsating current passes) will spin the rotor. In this method of spinning the rotor, the axes of the stator coils 3.3 and their ferromagnetic cores 3.4 can be aligned with or tilted with respect to the symmetry axis of the rotor. What matters here is the efficient penetration of the magnetic field fluxes of the coils into the cage of the rotor.

Figure 5:
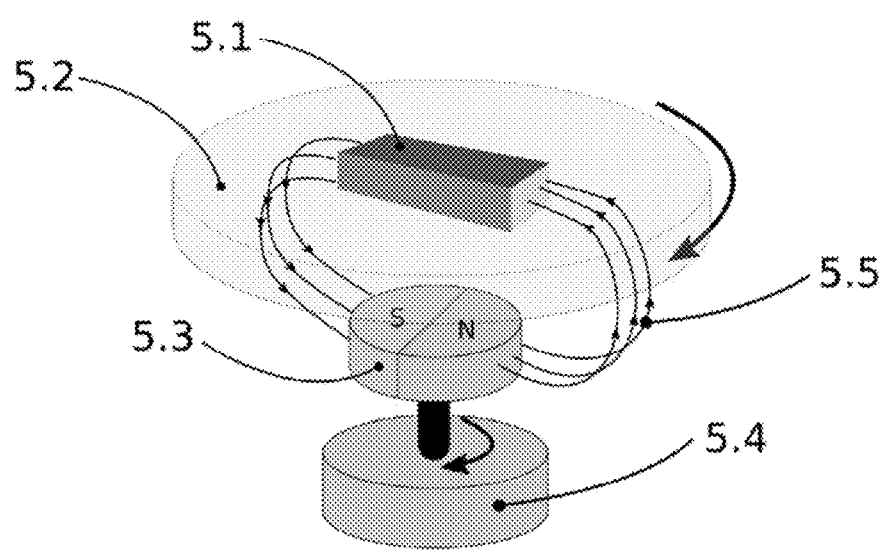
FIG. 5 presents a schematic view of a rotor with an elongated ferromagnetic core 5.1. An external magnet 5.3 is rotated using motor 5.4 and consequently spins the main disk 5.2. Magnetic field lines 5.5 of the permanent magnet 5.2 penetrate into the elongated ferromagnetic core 5.1 and lock the ferromagnetic core 5.1 to the permanent magnet.

The other method of rotating the rotor without using permanent disk magnet 2.3 is to use an elongated ferromagnetic core 5.1 inside the main disk 5.2 as shown in FIG. 5. The elongated ferromagnetic core 5.1 will follow the external magnetic field of magnet 5.3 rotated by motor 5.4 and spin together with the main disk 5.2. The magnetic field 5.5 of the permanent magnet 5.3 penetrates into the elongated ferromagnetic core 5.1, locking its rotation to the rotating magnet 5.3. In the absence of sufficient hydrodynamic levitation, however, this technique is likely to cause a direct contact between the rotor and its chamber, generating dry friction, heat and noise. Nonetheless, this method of spinning the rotor eliminates the permanent magnet from the rotor and reduces its manufacturing costs.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A micro rotary pumping system for pumping a fluid though the use of an external rotating magnetic field, comprising
    a micro channel for directing the fluid;
    a chamber located adjacent to said micro channel in fluid communication with said micro channel;
    an annular disk located in said chamber;
    said annular disk being rotationally stabilized within said chamber by the fluid between said annular disk and said chamber; and
    a magnetic material affixed to said annular disk and magnetically coupled to the external rotating magnetic field for rotating said annular disk to create a shear in the fluid in said micro channel for pumping the fluid thereby.

2. A micro rotary pumping system for pumping a fluid as set forth in claim 1, wherein said chamber is a substantially cylindrical chamber; and
    said micro channel intersecting a peripheral region of said cylindrical chamber.

3. A micro rotary pumping system for pumping a fluid as set forth in claim 1, wherein said chamber is a substantially cylindrical chamber; and
    said annular disk being embedded and sealed in said substantially cylindrical chamber.

4. A micro rotary pumping system for pumping a fluid as set forth in claim 1, wherein said micro channel has a range from 5 µm to 500 µm wide and said chamber having a range from 100 µm to 10 mm in diameter.

5. A micro rotary pumping system for pumping a fluid as set forth in claim 1, wherein said channel has a longitudinal axis perpendicular to an axis of rotation of said annular disk.

6. A micro rotary pumping system for pumping a fluid as set forth in claim 1, wherein said annular disk defines a substantially smooth cylindrical circumference.

7. A micro rotary pumping system for pumping a fluid through the use of an external rotating magnetic field, comprising:
a micro channel for directing the fluid;
a chamber located adjacent to said micro channel in fluid communication with said micro channel;
an annular disk located in said chamber;
said annular disk being void of a rotational axle and rotationally stabilized by the fluid between said annular disk and said chamber; and
a magnetic material affixed to said annular disk and magnetically coupled to the external rotating magnetic field for rotating said annular disk to create a shear in the fluid in said micro channel for pumping the fluid thereby.

8. A micro rotary pumping system for pumping a fluid as set forth in claim 1, wherein said annular disk has a diameter between 10 micrometer and 10 millimeters.

9. A micro rotary pumping system for pumping a fluid as set forth in claim 1, wherein said magnetic material affixed to said annular disk comprises a permanent magnet.

10. A micro rotary pumping system for pumping a fluid as set forth in claim 1, wherein said magnetic material affixed to said annular disk comprises an elongated ferromagnetic core.

11. The method of pumping a fluid in a micro channel coupled to a fluid chamber, comprising the steps of:
providing an annular disk within the fluid chamber,
affixing a magnetic material to said annular disk, and
magnetically coupling said magnetic material to an external rotating magnetic field and thereby magnetically rotating said annular disk within the fluid chamber to rotationally stabilize the annular disk within the chamber by the action of a portion of the fluid between said annular disk and said chamber and exerting boundary shear stress on the fluid along the micro channel to induces a velocity gradient across the channel to generate the flow of the fluid within the micro channel.

12. The method of pumping a fluid in a micro channel as set forth in claim 11, wherein the step of magnetically rotating the annular disk includes magnetically coupling the annular disk to an external rotating magnetic field for rotating the annular disk.

13. The method of pumping a fluid in a micro channel as set forth in claim 11, wherein the step of magnetically rotating the annular disk includes contactless, brushless, external magnetic fields induced by a rotating and external permanent magnet.

14. The method of pumping a fluid in a micro channel as set forth in claim 11, wherein the step of magnetically rotating the annular disk includes contactless, brushless, external magnetic fields induced by sequentially energizing an external array of coils.

15. The method of pumping a fluid in a micro channel as set forth in claim 11, wherein the step of magnetically rotating the annular disk includes sequentially energizing an external array of coils for levitating and rotating the annular disk encapsulated within the chamber.

16. A micro rotary pumping system for pumping a fluid though the use of a external rotating magnetic field, comprising
a micro channel for directing the fluid;
a substantially cylindrical chamber intersecting a peripheral region of said cylindrical chamber in fluid communication with said micro channel;
an annular disk having a substantially smooth cylindrical circumference located in said chamber;
said annular disk embedded and sealed in said substantially cylindrical chamber;
said annular disk being rotationally stabilized within said chamber by the fluid between said annular disk and said chamber; and
a magnetic material affixed to said annular disk and magnetically coupled to the external rotating magnetic field for rotating said annular disk to create a shear in the fluid in said micro channel for pumping the fluid thereby.

* * * * *